United States Patent
Griffiths et al.

[11] Patent Number: 5,484,939
[45] Date of Patent: Jan. 16, 1996

[54] 2-SUBSTITUTED 5-CHLORIMIDAZOLES

[75] Inventors: Gareth Griffiths, Visp; René Imwinkelried, Brig-Glis; Jacques Gosteli, Basel, all of Switzerland

[73] Assignee: Lonza Ltd., Gampel/Valais, Switzerland

[21] Appl. No.: 208,956

[22] Filed: Mar. 11, 1994

Related U.S. Application Data

[63] Continuation-in-part of Ser. No. 203,582, Mar. 1, 1994.

[30] Foreign Application Priority Data

Mar. 12, 1993 [CH] Switzerland ................ 748/93

[51] Int. Cl.$^6$ ................................................ C07D 233/08
[52] U.S. Cl. ........................................ 548/343.1; 548/334.5
[58] Field of Search ............................. 548/343.1

[56] References Cited

U.S. PATENT DOCUMENTS

| | | | |
|---|---|---|---|
| 3,409,606 | 11/1968 | Lutz et al. ............... | 260/157 |
| 4,335,040 | 10/1982 | Furukawa et al. ............. | 424/273 |

FOREIGN PATENT DOCUMENTS

| | | |
|---|---|---|
| 0028834 | 5/1981 | European Pat. Off. . |
| 0365030 | 4/1990 | European Pat. Off. . |
| 0429257 | 5/1991 | European Pat. Off. . |
| 0479479 | 4/1992 | European Pat. Off. . |
| 0505098 | 9/1992 | European Pat. Off. . |
| 2804435 | 8/1978 | Germany . |
| 3145927 | 6/1983 | Germany . |
| 3330192 | 3/1985 | Germany . |

OTHER PUBLICATIONS

Watson, Synthetic Communications, 22 (20) 297 (1992).
R. Jacquier et al., Bull. Soc. Chim. France, (1971), p. 1040.
Watanabe et al., J. Hetero Chem., vol. 27, No. 3, (1990), pp. 711 to 716.
Lutz et al., J. Hetero. Chem., vol. 4, (1967), pp. 399 to 402.
Imbach et al., J. Hetero. Chem., vol. 4, (1967), pp. 451 to 452.
Brown et al., J. Chem. Soc., Perkins Trans. I, No. 7, (1980), pp. 2310 to 2315.
Boschelli et al., Heterocycles, vol. 35, No. 1, (1993), pp. 121 to 124.
Patent Abstracts of Japan, vol. 12, No. 117, (C–487), (Apr. 13, 1988).

*Primary Examiner*—Robert Gerstl
*Attorney, Agent, or Firm*—Fisher, Christen & Sabol

[57] ABSTRACT

The 2-substituted 5-chlorimidazoles of general formula:

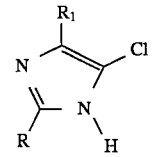

are new intermediate products for the production of antihypertensive pharmaceutical agents or of herbicidal compounds. A process for the production of these intermediate products as well as a new process for the further reaction of 2-substituted 5-chlorimidazoles of general formula I, wherein $R_1$ is hydrogen, to the 2-substituted 5-chlorimidazole-4-carbaldehydes of general formula:

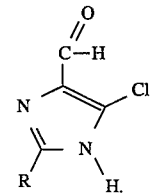

2 Claims, No Drawings

2-SUBSTITUTED 5-CHLORIMIDAZOLES

This is a continuation-in-part of U.S. Ser. No. 08/203,582, filed on Mar. 1, 1994.

BACKGROUND OF THE INVENTION

1. Field of the Invention

The invention relates to certain 2-substituted 5-chlorimidazoles, a process of preparing the 2-substituted 5-chlorimidazoles, and a process of converting some of the 2-substituted 5-chlorimidazoles to certain 2-substituted 5-chlorimidazole- 4-carbaldehydes.

2. Background Art

Several methods for the production of 2-substituted 5-chlorimidazole- 4-carbaldehydes are known.

U.S. Pat. No. 4,355,040 describes a process according to which 2-amino-3,3-dichloroacrylonitrile is reacted with an aldehyde to the corresponding azomethine intermediate product and further with an hydrogen halide and water to the 2-substituted 5-haloimidazole-4-carbaldehyde. Experimental data is lacking in the patent. A great drawback of the synthesis is that the 2-amino- 3,3-dichloroacrylonitrile used first has to be produced starting from dichloroacetonitrile by its reaction with hydrogen cyanide/sodium cyanide. The extremely toxic reactants and the safety measures associated therewith that are already necessary for the preparation of the initial product, make the entire process unsuitable for industrial-scale production.

U.S. Pat. No. 4,355,040 discloses in another variant a 3-stage process, in which, in a first stage, an amidinehydrochloride is cyclized with high $NH_3$ pressure with dihydroxyacetone, the imidazole alcohol is halogenated and finally oxidized to aldehyde.

It has turned out that pressures of over 20 bars are necessary for the cyclization reaction.

The oxidation of the alcohol works according to U.S. Pat. No. 4,355,040 in the presence of chromium oxide. It is obvious that an oxidation with heavy metal oxides, that are not recyclable as a rule, is no longer justifiable from present ecological aspects and requirements.

BROAD DESCRIPTION OF THE INVENTION

The main objective of the invention is to provide processes that do not have the above-mentioned drawbacks of the prior art. The main objective of the invention is achieved by the new 2-substituted 5-chlorimidazoles of the invention, a process for their production according to the invention and a process for the further reaction of the 5-chlorimidazole derivatives (wherein $R_1$ is H) to the corresponding carbaldehydes according to the invention.

Other objectives and advantages of the invention are set out herein or are obvious herefrom to one skilled in the art. The other objectives and advantages of the invention are achieved by the compounds and processes of the invention.

The invention includes 2-substituted 5-chlorimidazoles of the general formula:

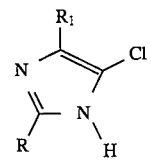

wherein R is hydrogen, an alkyl group, an alkenyl group, a cycloalkyl group, a benzyl group, a phenyl group or an aryl group, and $R_1$ is hydrogen, an alkyl group, a cycloalkyl group, a benzyl group, a phenyl group or an aryl group, or is $-CO_2R_3$ or $-(CH_2)_n-CO_2R_3$, wherein n is a numeral between 1 and 4 and $R_3$ is an alkyl group.

The invention also involves a process for the production of 2-substituted 5-chlorimidazoles of general formula I. The process includes, in the first stage, reacting a glycine ester hydrohalide of the general formula:

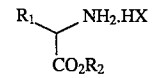

wherein $R_1$ has the above-mentioned meaning, R2 is an alkyl group and X is a halogen atom, in the presence of a base with an imidic acid ester of the general formula:

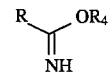

wherein R has the above-mentioned meaning and $R_4$ is an alkyl group, to the corresponding 3,5-dihydroimidazol-4-one of the general formula:

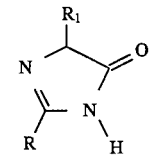

wherein R and $R_1$ have the above-mentioned meanings and, in the second stage, chlorinating the corresponding 3,5-dihydroimidazol- 4-one of the general formula V to the end product.

The invention further involves a process for the production of 2-substituted 5-chlorimidazole-4-carbaldehydes of the general formula:

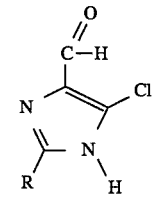

wherein R is hydrogen, an alkyl group, all alkenyl group, a cycloalkyl group, a benzyl group, a phenyl group or an aryl group. The process includes reacting a 2-substituted 5-chlorimidazole of the general formula I, wherein $R_1$ is hydrogen, with phosphoroxy chloride in the presence of N,N-dimethylformamide.

The 2-substituted 5-chlorimidazoles of the general formula I or the 2-substituted 5-chlorimidazole-4-carbaldehydes of the general formula II are important initial products for the production of antihypertensive pharmaceutical agents (U.S. Pat. No. 4,355,040) or of herbicial compounds (German OS 2804435).

DETAILED DESCRIPTION OF THE INVENTION

For the production of the 2-substituted 5-chlorimidazoles of general formula I according to the invention, in the first stage a glycine ester hydrohalide of general formula:

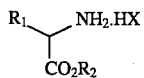

wherein $R_1$ has the above-mentioned meaning, $R_2$ is an alkyl group and X is a halogen atom, is reacted with an imidic acid ester of general formula:

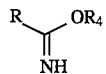

wherein R has the above-mentioned meaning and $R_4$ is an alkyl group, in the presence of a base to the corresponding 2-substituted 3,5-dihydroimidazol-4-one of general formula:

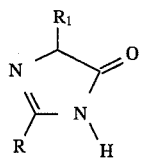

wherein R and $R_1$ have the above-mentioned meanings.

In the general substituents R, $R_1$, $R_2$, $R_3$ and $R_4$ the indicated groups have the following meanings:

An alkyl group is a straight-chain or branched $C_1$–$C_6$-alkyl group which is understood to be, such as, methyl, ethyl, n-propyl, isopropyl, n-butyl, sec.-butyl, tert.-butyl, pentyl or hexyl groups. The preferred alkyl group is one of the mentioned $C_1$–$C_4$-alkyl groups. The n-butyl group is preferred for substituent R.

An alkenyl group is a straight-chain or branched $C_1$–$C_6$-alkenyl group which is to be understood, such as, 1-propenyl, 2-propenyl, 1-butenyl, 2-butenyl, 3-butenyl, pentenyl and its isomers or hexenyl and its isomers. The 2 or 3-butenyl group is preferred for R.

Representatives of cycloalkyl groups are cyclopropyl, cyclobutyl, cyclopentyl or cyclohexyl groups.

Both the benzyl group and the phenyl group can contain substituents, such as, the above-mentioned alkyl groups, halogen atoms, nitro groups or amino groups.

Suitably chlorine, bromine or iodine, preferably chlorine, is understood under the designation halogen.

Suitably the procedure is that the glycine ester hydrohalide of general formula III is reacted in the presence of a base suitably at a pH of 7 to 12, preferably 9 to 11, with the imidic acid ester of general formula IV. The glycine ester hydrohalides of general formula III are commercially obtainable stable compounds. Suitable bases are the alkali hydroxides, such as, sodium hydroxide or potassium hydroxide or alkali alcoholates such as, sodium or potassium methylate, ethylate or tert. butylate. Advantageously the base is available dissolved in a suitable solvent. Especially suitable solvents are aliphatic alcohols such as methanol or ethanol. The imidic acid ester is suitably also added in the form of a solution in an inert solvent. Generally aromatic solvents are especially well suited for this purpose (i.e., the inert solvent), such as, toluene or chlorobenzene or the above-mentioned aliphatic alcohols.

Advantageously the reaction of the reactants glycine hydrohalide, imidic acid ester and base takes place in the stochiometric ratio of 1:1:1. The reaction temperature suitably ranges in the area of –20° C. to 50° C., preferably at 0° C. to 25° C.

After a reaction time of a few hours, the corresponding 2-substituted 3,5-dihydroimidazol-4-one of general formula V can be isolated by one skilled in the art, generally by simple filtration, in yields greater than 95 percent.

Advantageously the resulting reaction mixture is prepared without isolation of the 2-substituted 3,5-dihydroimidazol-4-one for further processing to the corresponding 5-chlorimidazole (one-pot process).

This first stage of the process according to the invention contains a tremendous improvement of the known process according to R. Jacquier et al., Bull. Soc. Chim. France, (1971), 1040, which comprises the reaction of the free glycine ester with an imidic acid ethyl ester in the absence of a solvent to the corresponding 3,5-dihydroimidazol-4-one. Disadvantageous in this known process is the fact that the free glycine ester is very unstable and therefore in each case must be newly synthesized and isolated for every reaction. According to the known process, after a reaction time of 24 hours and more, yields of only 30 to 48 percent could be obtained.

In the second stage, the 2-substituted 3,5-dihydroimidazol-4-one of general formula V is chlorinated to the corresponding 2-substituted 5-chlorimidazole of general formula I. Suitably the chlorination takes place with thionyl chloride or phosphoroxy chloride, advantageously in an excess of chlorinating agent of 10 to 300 percent at a reaction temperature in the range between 20° C. and 110° C. In this case the chlorinating agent can serve at the same time as the solvent so that generally an additional solvent is not necessary. Preferably phosphoroxy chloride is used as the chlorinating agent. The resultant 2-substituted 5-chlorimidazole of general formula I can be isolated in high purity from the reaction mixture in ways known to one skilled in the art, preferably by extraction.

Preferred 2-substituted 5-chlorimidazoles of general formula I are those in which R is n-butyl, 2-butenyl or 3-butenyl.

Initial compounds for the further reaction according to the invention to the 2-substituted 5-chlorimidazole-4-carbaldehyde of general formula II is a 2-substituted 5-chlorimidazole in which $R_1$ necessarily is hydrogen. The reaction to the desired 2-substituted 5-chlorimidazole-4-carbaldehyde of general formula II takes place according to the invention with phosphoroxy chloride or phosgene in the presence of N,N-dimethylformamide. Suitably the molar ratio of the reactants 2-substituted 5-chlorimidazole to phosphoroxy chloride or phosgene to N,N-dimethylformamide is in the range between 1:1:1 and 1:5:5, preferably at approximately 1:3:3. The reaction temperature is suitably between 50° C. and 130° C. Optionally in the presence of an additional inert solvent, it is possible in the one-pot process to work advantageously in the solvent of the first stage.

The isolation of the resultant 2-substituted 5-chlorimidazole-4-carbaldehyde from the reaction mixture takes place advantageously in ways known to one skilled in the art by its extraction with a suitable solvent.

EXAMPLES

Production of 2-n-butyl-3,5-dihydroimidazol-4-one 31.71 g (0.25 mol) of glycine methyl ester hydrochloride was added to a solution of 10.1 g (0.25 mol) of sodium hydroxide in methanol at 0° C. After 15 minutes, 126.5 g of a 22.8 percent solution of pentanimidic acid methyl ester in chlorobenzene was instilled for 5 minutes to a white suspension. The light yellow suspension was stirred for 4 hours at room temperature and diluted with chlorobenzene (100 ml). The methanol was distilled off at a temperature of 26° C. and a pressure of 30 to 50 mbar, and the orange suspension was diluted with methylene chloride (100 ml) and then filtered. After removal of the solvent from the filtrate, 34.08 g (97 percent) of the title compound (content>95 percent, according to GC and 1H-NMR) was obtained.

Production of 2-n-butyl-5-chlor-1H-imidazole 2-n-Butyl-3,5-dihydroimidazol-4-one (14.02 g, 0.1 mol) was added in portions for 15 minutes to POCl$_3$ (50 ml) at 95° C. The solution was heated for 2 hours at 100° C., cooled and poured on 400 g of ice. The mixture was adjusted to pH 7 with 255 ml of 30 percent sodium hydroxide solution and extracted three times with 500 ml of ethyl acetate each. The combined organic phases were dried with MgSO$_4$, filtered and concentrated by evaporation on a Rotavapor. After purification of the residue by column chromatography the title compound (5.52 g, 34.7 percent) was obtained in a high yield (>98 percent, according to GC and $^1$H-NMR). The product had a melting point of 85° to 87° C. Other data regarding the product was:

$^1$H-NMR (CDCl$_3$) δ 0.91 (3H, t, J=7.5 Hz), 1.36 (2H, sextet, J=7.5 Hz), 1.68 (2H, q, J=7.5 Hz), 2.70 (2H, t, J=7.5 Hz), 6.83 (1H, s), 10.65 (1H, br s).

Production of 2-n-butyl-5-chlorimidazole-4-carbaldehyde from 2-n-butyl- 5-chlor-1H-imidazole N,N-dimethylformamide (1.46 g, 20 mmol) was instilled in a solution heated to 95° C. of 2-n-butyl-5-chlor-1H-imidazole (1.60 g, 10 mmol) in POCl$_3$ (3.07 g, 20 mmol) and chlorobenzene (20 ml). The mixture was stirred for 3.5 hours at 98° C. Then further portions of POCl$_3$ (1.53 g, 10 mmol) and N,N-dimethylformamide (0.73 g, 10 mmol) were instilled. After another 2.5 hours at 98° C. the mixture was cooled and poured on ice (40 g). After 15 minutes the mixture was adjusted to pH 7 with 11 ml of 30 percent sodium hydroxide solution and extracted three times with 100 ml of ethyl acetate each. The combined organic phases were dried with MgSO4, filtered and concentrated by evaporation. The title compound was obtained in a yield of 1.3 g (70 percent).

What is claimed is:

1. A 2-substituted 5-chlorimidazole of the formula:

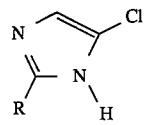

wherein R is 2-butenyl.

2. A 2-substituted 5-chlorimidazole of the formula:

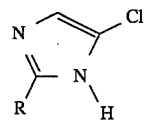

wherein R is 3-butenyl.

* * * * *